United States Patent [19]

Rowson et al.

[11] Patent Number: 4,508,659

[45] Date of Patent: Apr. 2, 1985

[54] 2-CYANO-3-BENZYLAMINO-2-PROPENO-ATES, USEFUL AS FUNGICIDES

[75] Inventors: Graham P. Rowson, Gt. Chesterford; Albert Percival, Hauxton; Philip N. Judson, Linton, all of England

[73] Assignee: FBC Limited, Hauxton, England

[21] Appl. No.: 470,679

[22] Filed: Feb. 28, 1983

[30] Foreign Application Priority Data

Mar. 5, 1982 [GB] United Kingdom ............... 8206480

[51] Int. Cl.³ .................. C07C 121/52; A61K 31/275
[52] U.S. Cl. ................................................ 260/465 D
[58] Field of Search .................... 260/465 D; 424/304

[56] References Cited

U.S. PATENT DOCUMENTS 3,723,498  3/1973  Joos ................................. 260/465.4
4,154,599  5/1979  Hedrich ................................. 71/98

OTHER PUBLICATIONS

Shvo et al., J.A.C.S., vol. 91, 6689 (1969).
Eiden, "Condensation of Acid Amides with Active Methylene Compounds and the Preparation of Thiazole Derivatives", Chemical Abstract 58:4564h (1963).

*Primary Examiner*—Nicky Chan
*Assistant Examiner*—C. Joseph Faraci
*Attorney, Agent, or Firm*—Lawrence Rosen

[57] ABSTRACT

Fungicidal compositions comprise a compound of formula I

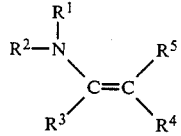

in which
$R^1$ and $R^3$ are hydrogen, alkyl or alkenyl;
$R^2$ is alkyl optionally substituted by a 5 or 6 membered oxygen containing ring or by phenyl (optionally substituted) and one of $R^4$ and $R^5$ is—CN and the other is a carboxylic ester or amide group. Many of the compounds are novel.

4 Claims, No Drawings

2-CYANO-3-BENZYLAMINO-2-PROPENOATES, USEFUL AS FUNGICIDES

The present invention relates to fungicidal compositions.

Many 2-cyano-2-propenoic acids and their derivatives are known including those having a 3-substituted amino group. We have found that a particular group of such compounds have fungicidal activity. Some of the compounds falling within this group have been described as for example in J.A.C.S. 1969, 91, 6689. We are not aware that these known compounds have been shown to have any pesticidal activity. Certain other 2-cyano-3-amino-2-propenoates have been described as having herbicidal activity (as in USP 4154599) but these are structurally quite different from the compounds of the present invention.

The present invention provides a fungicidal composition comprising a compound of formula I,

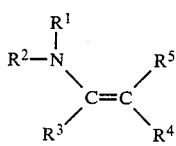

in which $R^1$ and $R^3$, which may be the same or different, are hydrogen, alkyl or alkenyl;

$R^2$ is alkyl, optionally substituted by a 5 or 6 membered oxygen containing ring or by phenyl (optionally substituted, e.g. by halogen, nitro, alkyl, haloalkyl or alkoxy), and one of $R^4$ and $R^5$ is —CN and the other is a carboxylic ester or amide group in association with an agronomically acceptable diluent or carrier.

According to the invention, we also provide, as new compounds, the compounds of formula I, where $R^1$ to $R^5$ are as defined above with the proviso that when $R^3$ is hydrogen, one of $R^4$ and $R^5$ is not —COOC$_2$H$_5$ or —COOCH$_3$.

The compounds and compositions of the invention are active against a range of fungal diseases, particularly those of plants, such as *Phytophthora infestans* (potato blight), *Plasmopara viticola* (vine downy mildew), *Pyricularia oryzae* (rice blast), *Erysiphe graminis* (barley powdery mildew), *Puccinia recondita* (wheat brown rust), and *Rhizoctonia solani*.

The present invention also provides a method of controlling or preventing fungal growth which comprises applying to a locus infested or liable to be infested by fungus a compound or composition according to the invention.

The locus infected or liable to be infected may be plants including tubers e.g. potatoes or seeds or their habitat such as the soil, aquatic areas, fabrics, textiles, paper, wood and the like.

The new compounds of formula I, may be prepared by reacting a compound of formula II $$R^1R^2NH \qquad II$$

with a compound of formula III

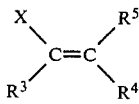

where $R^1$ to $R^5$ have the meanings given above and X is a leaving group, such as alkoxy or halogen e.g. chlorine. Compounds of formula III are generally known and may be prepared in any suitable manner. Where X is alkoxy the compound may be prepared by reacting a compound of formula IV $$R^5CH_2R^4 \qquad IV$$

with a trialkyl orthoester. This reaction can be combined with the reaction with compound II in a single stage process so that compound III is not isolated. Where the resulting product is one in which $R^1$ is hydrogen, this may if desired be alkylated or alkenylated with a suitable alkylating or alkenylating agent e.g. a dialkylsuphate under basic conditions or with an alkyl or alkenyl halide, usually in the presence of a base such as sodium hydride or carbonate.

The reaction of compounds II and III is generally carried out at a temperature of 50° to 150° C. (suitably under reflux) and preferably in a suitable solvent e.g. a lower alkanol, when X is alkoxy or, when X is a halogen, a hydrocarbon, such as toluene or an ether, such as tetrahydrofuran. When X is halogen, an acid acceptor is preferably present, e.g. K$_2$CO$_3$, or excess amine of formula III. When the reaction of compounds IV to III and III to I are combined the solvent may be an excess of trialkyl orthoester. This reaction is preferably carried out in the present of a catalytic amount of an acid, e.g. p-toluene sulphonic acid.

In the compounds of formula I we prefer each of $R^1$, $R^2$, $R^3$, $R^4$ and $R^5$, when they contain carbon, to contain less than 18, preferably less than 10, and more preferably less than 8, carbon atoms.

$R^5$ is preferably C$_{1-10}$ alkoxycarbonyl, especially C$_{3-5}$ alkoxycarbonyl. $R^3$ is preferably hydrogen.

A particularly preferred group of compounds are these in which $R^3$ is hydrogen, $R^1$ is methyl, $R^2$ is benzyl, $R^4$ is cyano and $R^5$ is C$_{3-5}$ alkoxycarbonyl.

Certain of the compounds of formula I may exist in stereoisomeric form and both isomeric forms of such compounds, and mixtures thereof, are included within the scope of this invention. In general the compounds are produced as a mixture of the two stereoisomeric forms.

The composition may of course include more than one compound of the invention.

In addition the composition can comprise one or more additional active ingredients, for example compounds known to possess herbicidal, fungicidal, insecticidal or acaricidal properties. Alternatively the compounds of the invention can be used in sequence with the other active ingredient. Fungicides which can be used in conjunction with the compounds of the present invention include maneb, zineb, mancozeb, thiram, ditalimfos, tridemorph, fenpropimorph, imazalil, propiconazole, triadimefon, triadimenol, diclobutrazol, fluotrimazole, ethirimol, fenarimol, nuarimol, triforine, pyracarbolid, tolclofos-methyl, oxycarboxin, carbendazim, benomyl, thiophanate, thiophanate-methyl, thiabendazole, propineb, metalaxyl, dicloran, dithianon, fuberidazole, dodine, chlorothalonil, cyprofuram, dichlofluanid, sulphur, copper compounds, iprodione, ziram, nabam, prochloraz (and metal complexes of these e.g. the manganese chloride complex), zineb-ethylene thiuramsulphide adduct, captan, captafol, benodanil, mepronil, carboxin, guazatine, validamycin, vinclozolin, tricyclazole, quintozene, pyrazophos, furmecyclox, propamocarb, procymidone, kasugamycin, furalaxyl, folpet, fenfuram, ofurace, etridiazole, fosethyl aluminium and benalaxyl.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The composition of the invention can take any form known in the art for the formulation of fungicidal compounds, for example, a solution, a dispersion, an aqueous emulsion, a dusting powder, a seed dressing, a fumigant, a smoke, a dispersble powder, an emulsifiable concentrate or granules. Moreover it can be in a suitable form for direct application or as a concentrate or primary composition which requires dilution with a suitable quantity of water or other diluent before application.

As a dispersion, the composition comprises a compound of the invention dispersed in a liquid medium, preferably water. It is often convenient to supply the consumer with a primary composition which can be diluted with water to form a dispersion having the desired concentration. The primary composition can be provided in any one of the following forms. It can be a dispersible solution which comprises a compound of the invention dissolved in a water-miscible solvent with the addition of a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsion comprises a compound of the invention dissolved in a water-immiscible solvent which is formed into an emulsion with water in the presence of an emulsifying agent. An emulsion of the desired concentration can be formed from a primary composition of the following types. A concentrated stock emulsion can be supplied comprising a compound of the invention in combination with an emulsifying agent, water and a water-immiscible solvent. Alternatively an emulsifiable concentrate can be supplied to the user comprising a solution of a compound of the invention in a water-immiscible solvent containing an emulsifying agent.

A dusting powder comprises a compound of the invention intimately mixed and ground with a soil pulverulent diluent, for example, kaolin.

A granular solid comprises a compound of the invention associated with similar diluents to those which may be employed in dusting powders, but the mixture is granulated by known methods. Alternatively it comprises the active ingredient adsorbed or absorbed on a pre-granular diluent, for example, Fuller's earth, attapulgite or limestone grit.

The concentration of the active ingredient in the composition of the present invention, is applied to plants is preferably within the range of 0.01 to 3.0 percent by weight, especially 0.5 to 3.0 percent by weight. In a primary composition the amount of active ingredient can vary widely and can be, for example, from 5 to 95 percent by weight of the composition.

In the method of the invention the compound is generally applied to seed, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid in the form of granules, or by applying the active ingredient at the same time as drilling by inserting it in the same drill as the seeds. A suitable application rate is within the range of from 0.05 to 20 kg per hectare, more preferably from 0.1 to 10 kg per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. For cereal crops such as wheat, barley and oats it is often desirable to spray the plant at or before growth stage 5 although additional treatments by spraying when the plant is more mature can augment resistance to the growth or spread of fungi. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 kg. per hectare, preferably from 0.05 to 5 kg. per hectare.

The invention is illustrated in the following Examples. Structures of novel compounds were confirmed by elemental and/or other appropriate analyses.

EXAMPLE 1

Isobutyl 3-(benzylmethylamino)-2-cyano-2-propenoate

This product was synthesised by one of two methods.

Method A

A mixture of isobutyl cyanoacetate (30 g), acetic anhydride (58 ml) and triethyl orthoformate (43 ml) was heated under reflux for 6 hours. The volatile material was evaporated and the residue was distilled to give isobutyl 2-cyano-3-ethoxy-2-propenoate, b.p. 130°–133° C./0.4 mm. A solution of this (6 g) in ethanol (30 ml) was mixed with benzylmethylamine (4 ml). The mixture was heated under reflux for 10 minutes and then cooled and diluted with water (50 ml). The solid was filtered and recrystallised from ethanol giving isobutyl 3-(benzylmethylamino)-2-cyano-2-propenoate, mp 105°–106° C.

Method B

Isobutyl cyanoacetate (5.8 g), benzylmethylamine (7 ml), triethyl orthoformate (14 ml) and p-toluenesulphonic acid (5 mg) were heated under reflux for 1 hour. The cooled reaction mixture was triturated with petroleum ether (bp 40°–60° C.) and the solid filtered off. Recrystallisation from ethanol gave isobutyl 3-(benzylmethylamino)-2-cyano-2-propenoate, m.p. 105°–106° C.

EXAMPLES 2–31

The following were prepared by similar methods $$\begin{array}{c} R^2 \\ \diagdown \\ N-CH=C \\ \diagup \\ R^1 \end{array} \begin{array}{c} COR^6 \\ \diagup \\ \diagdown \\ CN \end{array}$$

| EX. NO. | $R^2$ | $R^1$ | $R^6$ | METHOD | MP (°C.) |
|---|---|---|---|---|---|
| 2 | $PhCH_2$ | Me | $OPr^i$ | A | 54–55 |
| 3 | $PhCH_2$ | H | $OBu^n$ | A | 93–95 |
| 4 | $PhCH_2$ | Me | $OBu^n$ | A | 59–61 |
| 5 | $PhCH_2$ | Me | $NHPr^n$ | B | 135–137 |
| 6 | $Bu^n$ | Me | $OBu^n$ | A | Oil |
| 7 | $PhCH_2$ | H | NHEt | B | 132–135 |
| 8 | $PhCH_2$ | H | NHMe | B | 135–137 |
| 9 | $PhCH_2$ | Me | OMe | A | 72–74 |
| 10 | $Bu^n$ | Me | $OBu^i$ | A | 41–43 |
| 11 | $PhCH_2$ | Me | $OCH_2Bu^t$ | B | 42–43 |
| 12 | $PhCH_2$ | Me | cyclopentyloxy | B | 104–107 |
| 13 | $PhCH_2$ | Me | $OBu^s$ | B | 44–46 |
| 14 | $PhCH_2$ | Me | NHEt | B | 144–146 |
| 15 | $PhCH_2$ | Me | $OBu^i$ | B | 71–74 |
| 16 | $PhCH_2$ | Me | $OPr^n$ | B | 51–53 |
| 17 | $PhCH_2$ | Me | $OC_5H_{11}$ | B | 51–53 |
| 18 | $3,4Cl_2-C_6H_3CH_2$ | Me | OEt | B | 86–88 |
| 19 | $3NO_2-C_6H_4CH_2$ | Me | $OBu^i$ | B | 137–140 |
| 20 | $2Cl-C_6H_4CH_2$ | Me | $OPr^i$ | B | 74–76 |
| 21 | $2Cl-C_6H_4CH_2$ | Me | $OCH_2Bu^t$ | B | 85–87 |
| 22 | $2Cl-C_6H_4CH_2$ | Me | $OCH_2-CH=CH_2$ | B | 72–74 |
| 23 | $2Cl-C_6H_4CH_2$ | Et | OEt | B | 82–84 |
| 24 | $4Cl-C_6H_4CH_2$ | Me | OEt | B | 83–84 |
| 25 | $3,4Cl_2-C_6H_3CH_2$ | Me | $OBu^i$ | B | 121–123 |
| 26 | $2Me-C_6H_4CH_2$ | Me | $OBu^i$ | B | 103 |
| 27 | $PhCH_2$ | $Pr^i$ | $OBu^i$ | B | oil |
| 28 | $PhCH(Me)-$ (D-isomer) | H | $OBu^i$ | B | oil |
| 29 | $PhCH(Me)-$ (L-isomer) | H | $OBu^i$ | B | oil |
| 30 | $4Me_2N-C_6H_4CH_2$ | Me | $OBu^i$ | B | 94 |
| 31 | $PhCH_2$ | Et | $OBu^i$ | B | oil |

EXAMPLE 32

Using method A, there was obtained isobutyl 3-(furfurylamino)-2-cyano-2-propenoate, mp. 85°–87° C. This product (5 g) was treated with acetone (25 ml), potassium carbonate (6.1 g) and dimethylsulphate (2.1 ml). The mixture was heated under reflux for 20 hours with stirring. After cooling the slurry was poured into water and allowed to stand for 30 minutes in ice. The solid was filtered off and recrystallised from cyclohexane to give isobutyl 3-(furfurylmethylamino)-2-cyano-2-propenoate, mp 42°–44° C.

EXAMPLE 33

Using method B there was obtained isobutyl 3-(benzylmethylamino)-2-cyano-3-methyl-2-propenoate, as an oil.

EXAMPLE 34 AND 35

Using the method described in Example 32 the products of Examples 28 and 29 are methylated to give D-isobutyl 3-[(1-phenylethyl)methylamino)]-2-cyano-2-propenoate and the corresponding L-isomer, both obtained as oils.

EXAMPLE 36

This example illustrates a modified process for the preparation of the product of Example 1.

Triethyl orthoformate (11 mole) and benzylmethylamine (10 mole) were added dropwise, from separate funnels to a stirred solution of isobutyl cyanoacetate (10 mole) in isobutanol (31) containing p-toluenesulphonic acid (0.5 g) heated under reflux. The pot was maintained at 110°–150° C. Ethanol and isobutanol were distilled slowly whilst the temperature at the head of distillation column was kept at 100° C., the temperature being controlled by the rate of addition of triethyl orthoformate. When the addition was complete, the mixture was cooled to 80° C. and industrial methylated spirit (2½ l) added. The mixture was cooled with ice, the product filtered off and reslurried with industrial methylated sprit to give the desired product as a white solid.

EXAMPLE 37

A two week old maize meal/sand culture of the damping-off disease organism, Rhizoctonia solani, was thoroughly mixed by hand with clean sterile John Innes No 1 potting compost in the ratio of 1.5 g culture to 14 liters of soil. This infested soil was then left for approx. 18 hours before use. Compounds under test were each ground together with polyoxyethylene sorbitan monolaurate wetting agent (125 mg per liter of final volume), until a solution or fine suspension was produced, which was then diluted with distilled water to give dispersions containing various concentrations of active ingredient. 15 ml aliquots of these dispersions were added to 75 g portions of the infested soil which were contained in plastic cartons, 60 mm diameter×55 mm high.

Fifteen cabbage seeds, (variety Flower of Spring), were placed in a circular depression in the treated infested soil, re-covered, and the whole sealed with a plastic cap. The cartons were then placed in a constant temperature room at 22° C. At least two replications per treatment were made, with one additional treatment where seeds were sown in soil which was chemically treated only, i.e. there was no infestation. This latter treatment was included to measure the direct effect of the chemical on the germination of the seed.

After six days, the cartons were removed from the controlled temperature chamber and assessed for percentage disease control (calculated from seedling emergence).

The products of Examples 1, 2, 4, 6, 10–17, 19, 21, 22 25 and 32 gave greater than 50% control of the disease, at a concentration of 300 parts by weight of compound or less per million parts by volume of soil.

EXAMPLE 38

Aqueous acetone suspensions of the compound under test, at various concentration, containing 125 mg per liter of polyoxyethylene sorbitan monolaurate wetting agent, were applied to the leaves (sprayed to "run-off") and to the soil surrounding the roots (1 ml liquid/25 ml soil) of vine plants (*Vitis vinifera*) having 5 fully expanded leaves. The treated plants together with controls, treated with aqueous solutions of wetting agent only, were inoculated 24 hours later by spraying the leaves to "run-off" with an aqueous suspension of the sporangia of vine downy mildew (*Plasmopara viticola*). The plants were then placed in an atmosphere of 100% relative humidity at a temperature of 14°–18° C. for twelve days after which the disease control was assessed.

The products of Examples 2, 3, 6, 8, 9, 11, 13, 14, 17, 18, 21, 23 and 24 gave greater than 50% control of the disease compared with the controls, at a concentration of 2000 ppm (w/v) or less.

EXAMPLE 39

Aqueous acetone suspensions of the compound under test, at various concentrations, containing 125 mg per liter each of polyoxyethylene sorbitan monolaurate and ethylene oxide/propylene oxide block co-polymer wetting agents were applied to the soil surrounding the roots (1 ml liquid/25 ml soil) of rice plants (*Oryza sativa*) having 2 fully expanded leaves. The treated plants together with controls, treated with aqueous solutions of wetting agent only, were inoculated 24 hours later by spraying the leaves to "run-off" with an aqueous suspension of the spores of rice blast (*Pyricularia oryzae*). The plants were then placed in an atmosphere of 100% relative humidity at a temperature of 28° C. for seven days after which the disease control was assessed.

The products of Examples 3–5, 7, 11, 13, 14, 16, 17, 19 and 32 gave greater than 50% control of the disease compared with the controls, at a concentration of 2000 ppm (w/v).

EXAMPLE 40

In a similar manner to Example 39 compounds were tested for activity against potato blight (*Phytophthora infestans*) on potato plants (*Solanum tuberosum*) having 7 fully expanded leaves. The products of Examples 2, 6, 9, 10, 20 and 24 gave greater than 50% control of the disease compared with the controls, at a concentration of 2000 ppm (w/v) or less

EXAMPLE 41

Compositions were formulated as follows:

| (a) | Wettable powder | % w/w |
|---|---|---|
| | Compound of Example 1 | 50 |
| | Sodium dioctylsulphosuccinate | 3 |
| | Sodium lignosulphonate | 5 |
| | China clay | 42 |
| (b) | Aqueous flowable concentrate | % w/v |
| | Compound of Example 1 | 40 |
| | Sodium lignosulphonate | 2 |
| | Pluronic P75 (block copolymer of ethylene and propylene oxide) | 3 |
| | Dow Corning 1520 silicone antifoam | 0.1 |
| | Kelyan (Polysaccharide) | 0.2 |
| | Formaldehyde (40% aqueous solution) | 0.2 (v/v) |
| | Propylene glycol | 10.5 |
| | Water | to 100 |
| (a) | Dust | % w/w |
| | Compound of Example 1 | 10 |
| | Silica | 5 |
| | Talc | 85 |

We claim:

1. A compound of formula I

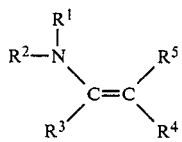

in which
R¹ is methyl;
R² is benzyl;
R³ is hydrogen;
R⁴ is cyano and
R⁵ is C$_{3-5}$ alkoxycarbonyl.

2. A compound according to claim 1 which is isobutyl 3-benzylmethylamino-2-cyano-2-propenoate.

3. A fungicidal composition which comprises a fungicidally effective amount of a compound as claimed in claim 1.

4. A method of controlling or preventing fungal growth which comprises applying to a locus infested or liable to be infested by a fungus, a fungicidally effective amount of a compound as claimed in claim 1.

* * * * *